United States Patent [19]
Levy

[11] Patent Number: 6,006,911
[45] Date of Patent: Dec. 28, 1999

[54] SPECIMEN SLIDE HOLDER WITH INTEGRAL CLOSURE FASTENER

[76] Inventor: Abner Levy, 325 N. Oakhurst Dr., P4, Beverly Hills, Calif. 90210

[21] Appl. No.: 09/172,117

[22] Filed: Oct. 13, 1998

[51] Int. Cl.[6] .............................. B65D 85/48; B65D 73/00
[52] U.S. Cl. ........................... 206/456; 206/474; 206/569
[58] Field of Search ..................... 206/456, 569, 206/474, 475, 476, 478, 482; 229/77, 84

[56] References Cited

U.S. PATENT DOCUMENTS

| | | | |
|---|---|---|---|
| D. 383,215 | 9/1997 | Levy | D24/225 |
| 1,391,287 | 9/1921 | Waldes | 206/482 X |
| 1,714,774 | 5/1929 | Goldsmith | 206/474 X |
| 2,050,270 | 8/1936 | Burnham | 206/475 X |
| 2,783,877 | 3/1957 | Volckering et al. | 206/474 |
| 4,334,611 | 6/1982 | Watson et al. | 206/474 X |
| 4,819,804 | 4/1989 | Levy | 206/456 |
| 4,976,359 | 12/1990 | Levy | 206/456 |
| 5,611,433 | 3/1997 | Levy | 206/569 |

Primary Examiner—Bryon P. Gehman
Attorney, Agent, or Firm—Natan Epstein Beehler & Pavitt

[57] ABSTRACT

A holder for medical specimen slides is made of a single sheet of corrugated cardboard cut and folded to make a tray portion and a cover portion hinged to each other for holding one or more slides therebetween. The holder features a tab integral with the cover which is pressed into a cutout in the tray portion to secure the holder in closed condition without need for external fasteners such as adhesive tape.

11 Claims, 2 Drawing Sheets

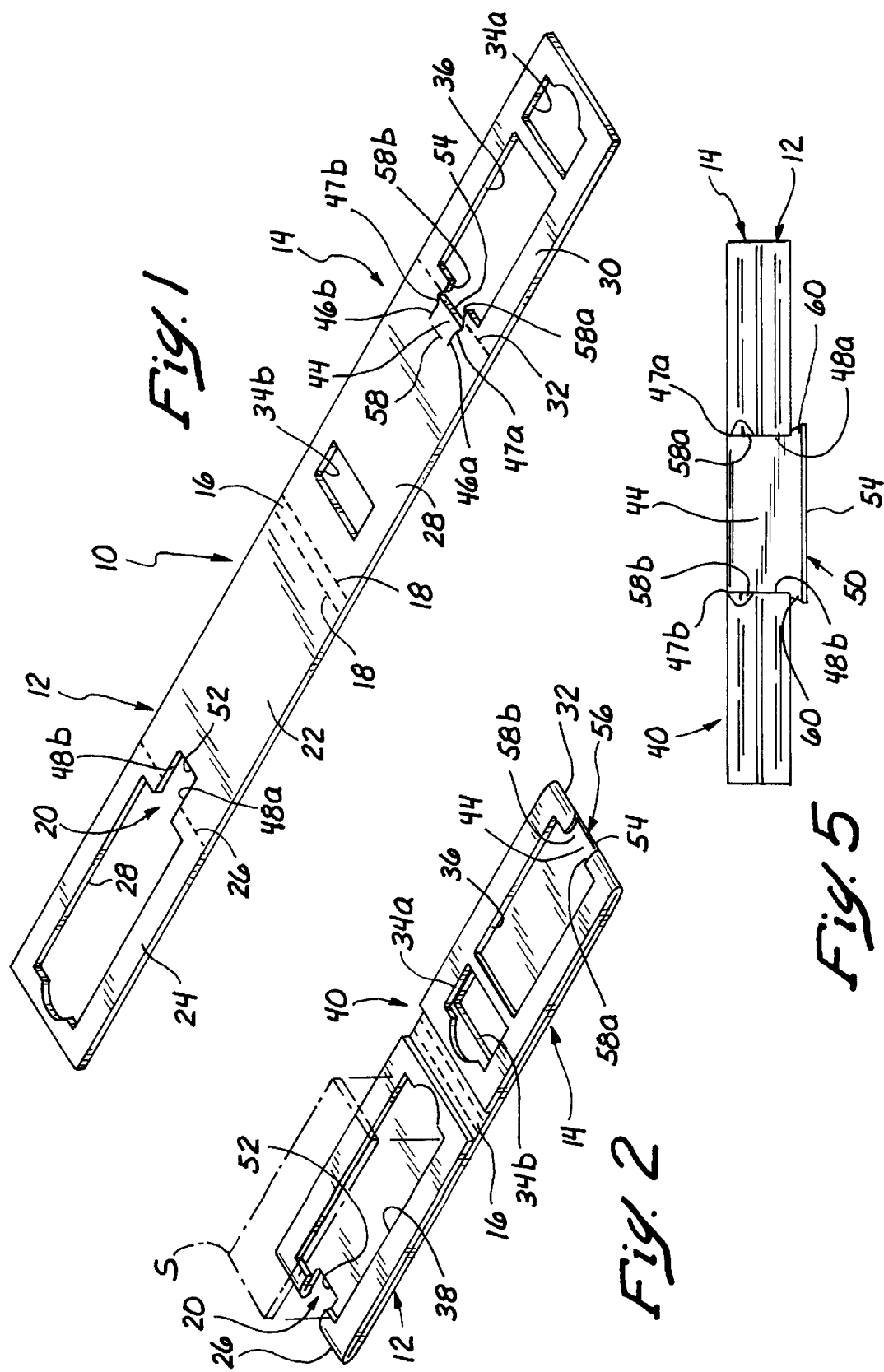

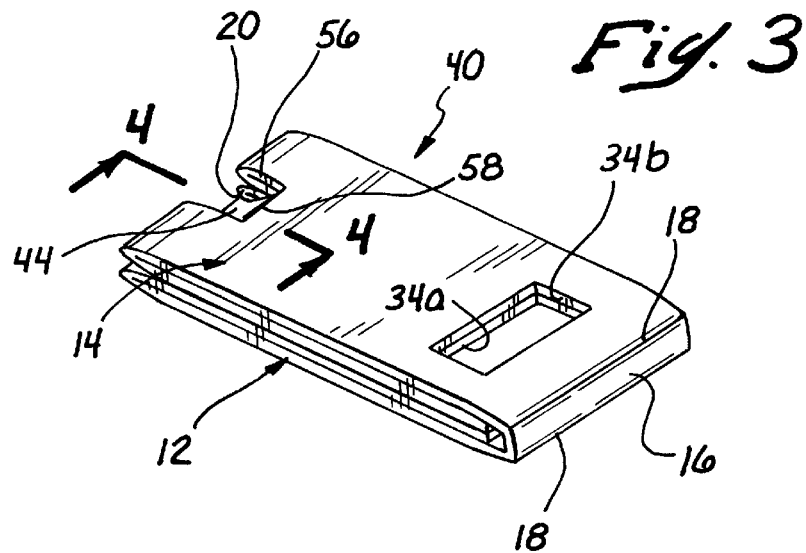
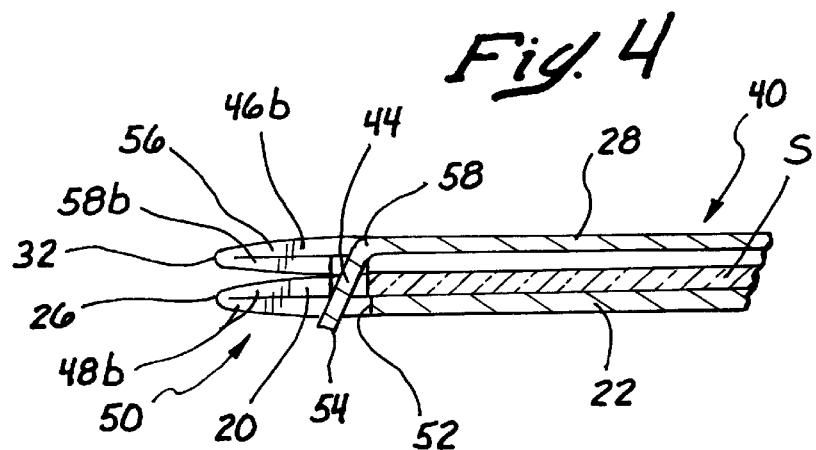
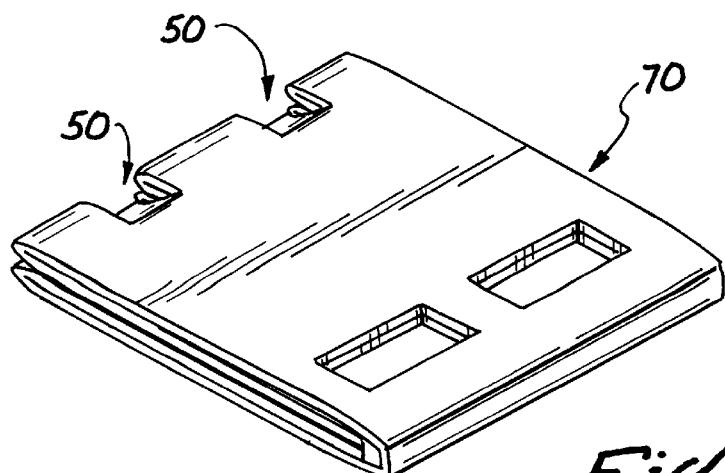

//6,006,911

SPECIMEN SLIDE HOLDER WITH INTEGRAL CLOSURE FASTENER

BACKGROUND OF THE INVENTION

1. Field of the Invention

This invention relates to the field of disposable holders and mailers of the type used for conveying medical specimen slides from a sample collection site to a clinical laboratory site, and in particular concerns such holders featuring an integral closure for keeping the slide holder closed.

2. State of the Prior Art

Medical specimens such as tissue and fluid samples are frequently collected slides on small strips of glass by an examining physician or medical technician and sent to a clinical laboratory for analysis. During transport it is necessary to protect the slide and the specimen material against loss and contamination. For this purpose various slide holders and mailers have been devised and are in widespread use. The mailers are typically designed to be disposable and are made of low cost materials such as cardboard or plastic. Cardboard slide holders are in particularly widespread usage because of their low cost and relative convenience and effectiveness. These are typically made of corrugated cardboard and are available in different sizes and configurations designed for holding different numbers of specimen slides, from a single slide to many slides.

Cardboard slide holders are manufactured by die cutting flat sheets of cardboard to make one-piece cardboard blanks which are then folded and glued to make the finished slide holder. The finished holder has a cover portion and a tray portion hinged to each other along a fold line of the blank. The specimen slide or slides are held between the tray and the cover when the holder is folded to a closed condition. In U.S. Pat. No. 5,611,433 which is incorporated by this reference as if fully set forth herein, this applicant disclosed an improved cardboard slide holder featuring a recess in the cover portion of the holder. The recess overlies the specimen bearing area of the slide preventing contact between the holder and the specimen. Conventional cardboard holders which lack the aforementioned feature also remain in common use. A shortcoming common to all these cardboard slide holders is the absence of any convenient means for keeping the holder closed during handling and transport. Presently this is accomplished by applying a piece of adhesive tape over the edges of the closed holder to keep it from opening. This requires the user to provide the piece of tape which is a significant inconvenience. Also, adhesive tape once removed does not adhere very well so that once the slide holder has been closed it cannot be reclosed without a fresh piece of tape. The tape is not easily removed and the most expedient method of opening the slide holder is by cutting the tape. In an effort to overcome some of these difficulties, some cardboard slide holders have been provided with patches of contact adhesive. These eliminate the need for providing a separate piece of tape but add significantly to the cost of the holder and normally require a covering of release sheet material which is removed to expose the adhesive just prior to closing the holder, making the holder more difficult to handle.

A continuing need exists for slide holders having a more convenient, reusable closure which does not add materially to the cost of the disposable slide holder.

SUMMARY OF THE INVENTION

The present invention provides a slide holder such as a corrugated cardboard slide holder with an integral fastener or closure which is made during the one step die cutting of the cardboard blank and requires neither additional manufacturing steps nor materials. The fastener is reliable, easy to use and can be opened and closed a number of times without appreciable loss of effectiveness.

The improved medical specimen slide holder according to this invention comprises a single sheet cut to define first and second holder portions, such as a slide tray and a cover, hinged to each other for containing therebetween one or more specimen slides in a folded condition of the holder. A closure fastener for securing the slide holder closed is defined by cutting fastener parts integrally with the first and second portion of the holder in an initially flat condition of the sheet. After the blank is folded to make the finished slide holder, one or more of the integral fastener parts are bent into retentive engagement with each other for securing the holder in folded closed condition. The integral fastener parts may comprise a tab integral with one of the portions and bendable into retentive engagement with retaining edges of a cutout defined in the other of the portions. The tab may be pressed into the cutout and is retained between the cutout edges in a bent condition transversely to the two portions of the holder thereby keeping the two portions of the slide holder together. Retention of the tab in locked position is enhanced by slightly widening the tab, for example by widening the free edge or end of the tab to provide small laterally projecting points or the like, so that the tab may still be pressed through the cutout but will then resist withdrawal from the cutout by making an interference fit with the edges of the cutout. In its bent, locked condition the end of the tab projects a small distance on one side of the holder so that it can be easily lifted with a finger and released from the cutout to permit opening of the slide holder. While this invention is not limited to the use of specific materials in the slide holder, the improvement disclosed herein will be found particularly useful with corrugated cardboard slide holders which already are in wide use. In that case, the single sheet is of corrugated cardboard having corrugations oriented so as to facilitate bending of the fastener tab into retentive engagement, i.e. with the corrugations parallel to the bend line of the fastener tab.

These and other improvements, features and advantages of the improved specimen slide holder of this invention will be better understood by reference to the following detailed description taken in conjunction with the accompanying drawings.

BRIEF DESCRIPTION OF THE DRAWINGS

FIG. 1 is a perspective view of a cardboard blank for a single slide holder with integral closure fastener according to this invention;

FIG. 2 shows the blank of FIG. 1 folded and glued to make the tray and cover portions, and illustrates in phantom lining a specimen slide holder positioned above the slide recess in the tray portion;

FIG. 3 show the specimen slide holder folded closed and the fastener tab depressed into locking position;

FIG. 4 is a sectional view taken along line 4—4 in FIG. 3 showing the closure fastener in locked position;

FIG. 5 is a left end view of the specimen slide holder of FIG. 4 showing the closure fastener in locked position; and FIG. 6 is a perspective view of a dual slide holder provided with two closure fasteners.

DETAILED DESCRIPTION OF THE PREFERRED EMBODIMENTS

With reference to the accompanying drawings in which like elements are designated by like numerals, FIG. 1 shows a blank 10 cut from a larger flat sheet of corrugated cardboard. The flat blank 10 includes a tray portion 12 and a cover portion 14 joined along a hinge strip 16 defined between fold lines 18. The tray portion has a bottom panel 22 and an inner panel 24 joined along fold line 26. A tray opening 28 is cut in the inner panel 24. The cover portion has an outer panel 28 and an inner panel 30 joined along fold line 32, two window openings 34a, 34b and a relief opening 36.

The finished specimen slide holder 40 is shown in FIG. 2 and is made by folding and gluing the inner panel 24 over the bottom panel 22, and the outer panel 28 over the inner panel 30. The tray opening 28 now defines a tray recess of depression which is sized to receive and hold a specimen slide S shown in phantom lining in FIG. 2. The window openings 28a, 28b align with each other in the folded cover portion to define a window 32 over an indicia bearing end area of the slide S when the holder is folded closed, to permit inspection of identifying markings applied to the area. Relief opening 30 defines a rectangular relief recess which overlies the specimen bearing area of slide S when the holder is folded closed. The relief recess accommodates specimen material placed on the slide S and avoids contact between the specimen and the holder when the cover portion is folded over the slide.

The slide holder 40 is improved by providing a closure fastener generally designated by numeral 50 and formed integrally with the blank 10 by making appropriate cuts in the blank. Blank 10 is typically cut in a one-step die cutting operation in a manner which is well known in the art. The integral parts which together constitute the closure fastener 50 are advantageously cut in the same one-step die cutting operation, with appropriate modification to the cutting die. The necessary modifications will be apparent to a skilled die maker from the present disclosure and need not be described here.

The integral parts of the fastener closure include a fastener tab 44 defined between cuts 46a, 46b, and an elongated cutout 20 defined by side edges 48a, 48b extending from the tray opening and across fold line 26 to terminate at inner edge 52. The tab 44 has a free edge 54 between cuts 46a, 46b which lies approximately along fold line 32. A cutout 56 between side edges 58a, 58b extends the relief opening 36 to the free edge 54 of the fastener tab.

In the finished slide holder 40 folded to a closed condition with the cover portion 14 facing up, as in FIGS. 3, 4 and 5, the tab 44 overlies, i.e., is in register with, both cutout 56 and also cutout 20. More specifically, the cuts 46a, 46b of the tab are approximately aligned with the side edges of the side edges 48a, 48b of cutout 20. Tab 44 can be pressed down and bent along a bend line 58 through cutout 56 and into cutout 20, as best understood by reference to FIG. 4. The width of the tab 44 along its free edge 54 is increased by divergents end segments 47a, 47b of cuts 46a, 46b which define laterally extending corners 60. Corners 60 project a small distance beyond the width of the cutout 56 and over the side edges 48a, 48b. When the tab 44 is fully depressed into locking position transversely to the tray portion 12 as shown in FIGS. 4 and 5 the free edge 54 with corners 60 pass entirely through cutout 20 and below the exterior side of the tray bottom panel 22. Although the corners 60 are bent inwardly during passage of the tab between the side edges 48a, 48b, the corners tend to spread out sideways because of inherent resilience of the sheet material once the end of the tab has cleared the side edges and passed below the bottom panel 22 where the corners are no longer laterally contained. Corrugated cardboard and similar materials have sufficient resilience for this purpose. The expanded corners then make an interference fit with the side edges 48a, 48b as best seen in FIG. 5 and retain the tab in locking engagement with the side edges of the cutout 56 on the tray portion 12. The side edges of the tab may also frictionally engage the side edges 48a, 48b of the cutout 56 to assist with retentive engagement. This retentive engagement of the tab 44 suffices to secure the tray and cover portions 12, 14 of slide holder 40 in closed condition during normal handling.

It will be appreciated that the tray and cover portions each include a double thickness of cardboard, each consisting of two overlapping panels of the folded single sheet 12. Specifically, tray portion 12 includes panels 22 and 24 while cover portion 14 includes panels 28 and 30. Similarly, the cutout 20 is cut through a double thickness 22,24 of the folded cardboard sheet so that the side edges 48a, 48b of the cutout each include a double thickness of corrugated cardboard. In the presently preferred embodiment of this invention, however, the locking tab 44 has only one thickness of cardboard. Another characteristic of the improved slide holder is that both the cover and tray portions are generally planar in an open condition of the holder and remain generally planar and mutually parallel in a closed condition of the holder as well, as may be readily seen in the drawings. Generally, the holder is held closed substantially entirely by the engagement of the tab 44 with the opposed side edges 48a, 48b of cutout 20.

The closure fastener 50 is easily released by lifting the tab out of the cutouts 20 and 56 out of retentive engagement with the tray portion 12. Release of the fastener 50 is facilitated by protrusion of the free edge 54 of the tab on one side of the holder 40, that is, below the tray portion as best seen in FIG. 5. The protruding end of the fastener tab is easily engaged with a fingertip and lifted through cutout 54 out of engagement with the tray portion 12.

The portion of cutout 20 between fold line 26 and inner edge 52 partially extends into the tray recess under one end of the specimen slide S, and admits part of a fingertip to facilitate lifting of the specimen slide out of the tray recess by pushing up the slide end with the fingertip through the recess 20.

It is contemplated that the closure fastener 50 will be particularly useful with specimen slide holders of corrugated cardboard which are in particularly widespread use. In such case it is best to orient the cardboard sheet so that the corrugations run parallel to the various fold lines 26, 18, 32 and the bend line of the fastener tab 44.

The invention is not limited however to any particular choice of materials and similar slide holders with the integral closure fastener can be made of cardboard, paper, and plastic materials, for example.

It should be further understood that the location of the fastener 50 need not be centered along the end of the slide holder opposite the hinged side 16. The fastener may be repositioned at any point around the slide holder although the fastener 50 is more effective when further from the hinged side. The invention is also not limited to a particular size or configuration of slide holder. By way of example, FIG. 6 illustrates a dual slide holder 70 made by a process analogous to that of the slide holder 40 described above. The dual holder 60 is essentially equivalent to two side-by-side holders 40 but made from a one-piece blank. The holder 60 has two closure fasteners 50 such as described above.

Also, the particular shape of the interlocking parts which constitute the fastener 50 may vary, and this invention encompasses any fastener comprised of integral parts defined by cutting a one-piece slide holder blank and which can be bent into retentive or interlocking engagement in the completed slide holder, regardless of the shape of these integral parts or their location on the slide holder.

While particular embodiments of the present invention have been described and illustrated for purposes of clarity and example, many changes, substitutions and modifications to the described embodiments will become apparent to those having ordinary skill in the art without thereby departing from the scope of this invention as defined by the following claims.

What is claimed is:

1. A medical specimen slide holder comprising:

a single sheet cut to define first and second portions hinged to each other for containing therebetween at least one specimen slide in a folded condition of said holder;

a cutout defined in one of said portions and a tab integral with the other of said portions, said cutout having opposite side edges on opposite sides of said tab in a locking condition of said holder, said cutout being sized to admit bending of the tab along a tab bend line transverse to said side edges into said locking condition for retaining said holder in said folded condition with both first and second portions in planar mutually parallel condition, said tab being retained in said locking condition substantially entirely by retentive engagement of said sides of said tab with said side edges.

2. The slide holder of claim 1 wherein said tab has a free edge wider than the width of said cutout between said side edges such that the tab is partially compressed between said opposite side edges when pressed through said cutout thereby to help retain said tab in said locking condition.

3. The slide holder of claim 2 wherein said free edge of said tab projects slightly from an exterior side of said other of said portions to facilitate lifting of the tab out of said cutout with a fingertip.

4. The slide holder of claim 2 wherein said tab has corner portions projecting in interference with said opposite side edges of the cutout thereby to retain the tab in said locking condition.

5. The slide holder of claim 1 wherein said cutout has an open end and said tab extends with a free tab end towards said open end.

6. The slide holder of claim 1 wherein said tab comprises a single thickness of said sheet and said side edges each include a double thickness of said sheet.

7. The slide holder of claim 1 wherein said retentive engagement includes frictional engagement between said sides of said tab and said side edges of the cutout.

8. The slide holder of claim 1 wherein said retentive engagement includes an interference fit between said tab and said side edges of the cutout.

9. The slide holder of claim 1 wherein said sheet is a sheet of corrugated cardboard.

10. A medical specimen slide holder comprising a single sheet of corrugated cardboard cut to define a tray portion and a cover portion hinged to each other for containing therebetween at least one specimen slide in a folded condition of said holder, each said tray portion and cover portion having a double thickness of said corrugated cardboard, a tab integral with one thickness of one of said tray and cover portions, a cutout defining opposed retaining edges through both thicknesses in the other of said tray and cover portions, said tab being bendable to a position transverse to said tray and cover portions, said tab being sized and configured to bend into said cutout along a tab bend line generally coincident with an inside edge of the cutout and engage in an interference fit with said side edges of said cutout for locking said holder in said folded condition with both tray and cover portions in planar mutually parallel position.

11. The slide holder of claim 10 wherein said cutout is generally rectangular, said tab has side edges which are partially divergent to define corner portions wider than said cutout, the tab being dimensioned and configured to pass between the side edges of the cutout when manually bent to a transverse position and to be retained by interference between said corner portions and edge portions of the cutout.

* * * * *